United States Patent

Morton et al.

[11] Patent Number: 6,077,350
[45] Date of Patent: Jun. 20, 2000

[54] SYSTEM AND METHOD FOR CURING POLYMERIC/PHOTORESIST COATINGS

[75] Inventors: Edward W. Morton, Turnersville; Robert Andrukaitis, Mantua; Joseph Scarpinato, Williamstown, all of N.J.

[73] Assignees: Sony Corporation, Tokyo, Japan; Sony Electronics, Park Ridge, N.J.

[21] Appl. No.: 09/037,366

[22] Filed: Mar. 10, 1998

[51] Int. Cl.[7] .......................... B05C 11/00; G01N 7/00; G01N 17/00; G01N 3/26; G05B 1/00
[52] U.S. Cl. ........................ 118/58; 118/688; 118/712; 73/23.2; 73/150 R; 374/53; 422/105; 436/55; 436/85
[58] Field of Search ........................ 118/58, 688, 690, 118/692, 712; 156/359; 73/23.2, 31.03, 31.05, 150 R, 150 A; 324/464; 374/53; 436/55, 85; 422/62, 105

[56] References Cited

U.S. PATENT DOCUMENTS

| | | | |
|---|---|---|---|
| 3,746,509 | 7/1973 | Koskan | 436/34 |
| 4,670,400 | 6/1987 | Leenders et al. | 436/34 |
| 5,525,051 | 6/1996 | Takano | 425/174.4 |
| 5,663,211 | 9/1997 | Kominami et al. | 522/8 |

*Primary Examiner*—Curtis Mayes
*Assistant Examiner*—J. A. Lorenzo
*Attorney, Agent, or Firm*—Gibbons, Del Deo, Dolan, Griffinger and Vecchion

[57] ABSTRACT

The present invention provides a system and method for thermally curing polymeric coated substrates by effective drying of solvents used in the production of the coated component. A feedback system coupled to a heating apparatus is comprised of one or more gas sensors internal or external to the heating apparatus to provide monitoring of the quantity of solvent gases being generated. The present invention allows the curing process to be precisely controlled, where, for example, a predetermined concentration of solvent gases input to the gas sensor can trigger the heating process to be stopped or to provide for a controlled cool down period for curing of the photoresist substrate. A controller coupled between the gas sensor and the heating apparatus may also contain temperature and/or time controls for varying the output of the heating apparatus in response to indications from the gas sensor. The system of the present invention assures production of stable photoresist coatings and also minimizes the processing time needed to properly cure the polymeric coated substrates.

21 Claims, 3 Drawing Sheets

6,077,350

SYSTEM AND METHOD FOR CURING POLYMERIC/PHOTORESIST COATINGS

FIELD OF THE INVENTION

The present invention relates generally to the fabrication of polymer coated substrates, and more particularly to a curing system for monitoring the drying process of photoresist coatings that are deposited on the substrates.

BACKGROUND OF THE INVENTION

Application of a fluid polymer coating onto a substrate is one necessary process in the manufacture of a great variety of electronic substrate components. As an example, a photoresist composition is applied to a substrate to fabricate glassmasters for the production of compact discs, semiconductor integrated circuits and other products. Typical liquid-type photoresist compositions used to coat these devices comprise a polymer and photosensitive compound dissolved or suspended in an organic solvent.

Other processing steps may be needed in addition to the polymeric coating. For example, in the production of a compact disc glassmaster, the glass surface of the substrate is thoroughly cleaned and dried prior to application of the photoresist coating. Glass, however, has a high affinity to water and a molecular layer of water will adhere to the surface. Water has a tendency to repel photoresist compositions when they are applied onto a water containing surface. In this case an intermediate adhesive layer is required which has a high affinity to the glass surface and to which the subsequently applied polymeric material has a reasonable affinity. The adhesive layer is preliminarily deposited on the surface of the substrate in an organic solvent prior to deposition of photoresist compositions. Additional layers of appropriate materials may be deposited on this substrate. Like the compact disc manufacturing industry, the production of semiconductors for certain applications requires a highly polished surface to be maintained prior to coating with a photoresist. A barrier layer is generally applied between the substrate, for example, silicon, alumina or quartz, and the polymeric photoresist.

Various methods for curing polymer and more specifically photoresist coatings, employing temperature or time control heating systems to fix the coating on the substrate are currently used. These curing/drying procedures are not always sufficiently effective in removing all the solvents in these coating processes. It is believed that the uncured or partially cured polymer coatings may cause failure of the substrate during additional processing steps or utilization of the product which is carried out after this development operation. Accordingly, there is a need for an improved curing system which more precisely monitors the curing process.

SUMMARY OF THE INVENTION

The present invention provides a system and method for thermally curing polymeric coated substrates by effectively controlling the drying of solvents used in the production of the coated component. In one exemplary embodiment of the present invention, a heating apparatus capable of producing sufficient heat to vaporize the solvent or solvents used for preparation of a polymer coated substrate is operated in conjunction with a feedback system coupled to the heating apparatus, and which is comprised of one or more gas sensors internal or external to the heating apparatus to provide monitoring of the quantity of solvent gases being generated. Use of the present invention allows the curing process to be precisely controlled, where, for example, a predetermined concentration of solvent gases input to the gas sensor can trigger the heating process to be stopped or to provide for a controlled cool down period for curing of the photoresist substrate. A controller coupled between the gas sensor and the heating apparatus may also contain temperature and/or time controls for varying the output of the heating apparatus in response to indications from the gas sensor. The system of the present invention assures production of stable photoresist coatings and also minimizes the processing time needed to properly cure the polymeric coated substrates.

BRIEF DESCRIPTION OF THE FIGURES

For a better understanding of the present invention, reference may be made to the following description of process steps and exemplary embodiments to be considered in conjunction with the accompanying drawings, in which.

DETAILED DESCRIPTION OF THE DRAWINGS

The present invention is a system and method for thermally curing polymeric coated electronic and other substrates by effective drying of solvents used in the production of the coated component. The drying of the solvents is precisely detected by employing a feedback mechanism which monitors vapor concentration of the evaporating solvent materials. Although the system and method of the present invention can be used in a wide variety of applications, such as the manufacture of circuit boards, liquid crystal displays, semiconductor integrated circuits and other products, the present invention system and method are particularly well suited for use in the fabrication of glassmasters utilized in the manufacture of compact discs. Accordingly, the system and method will be described with respect to an exemplary application involving production of glassmasters for compact discs.

Figure 1:
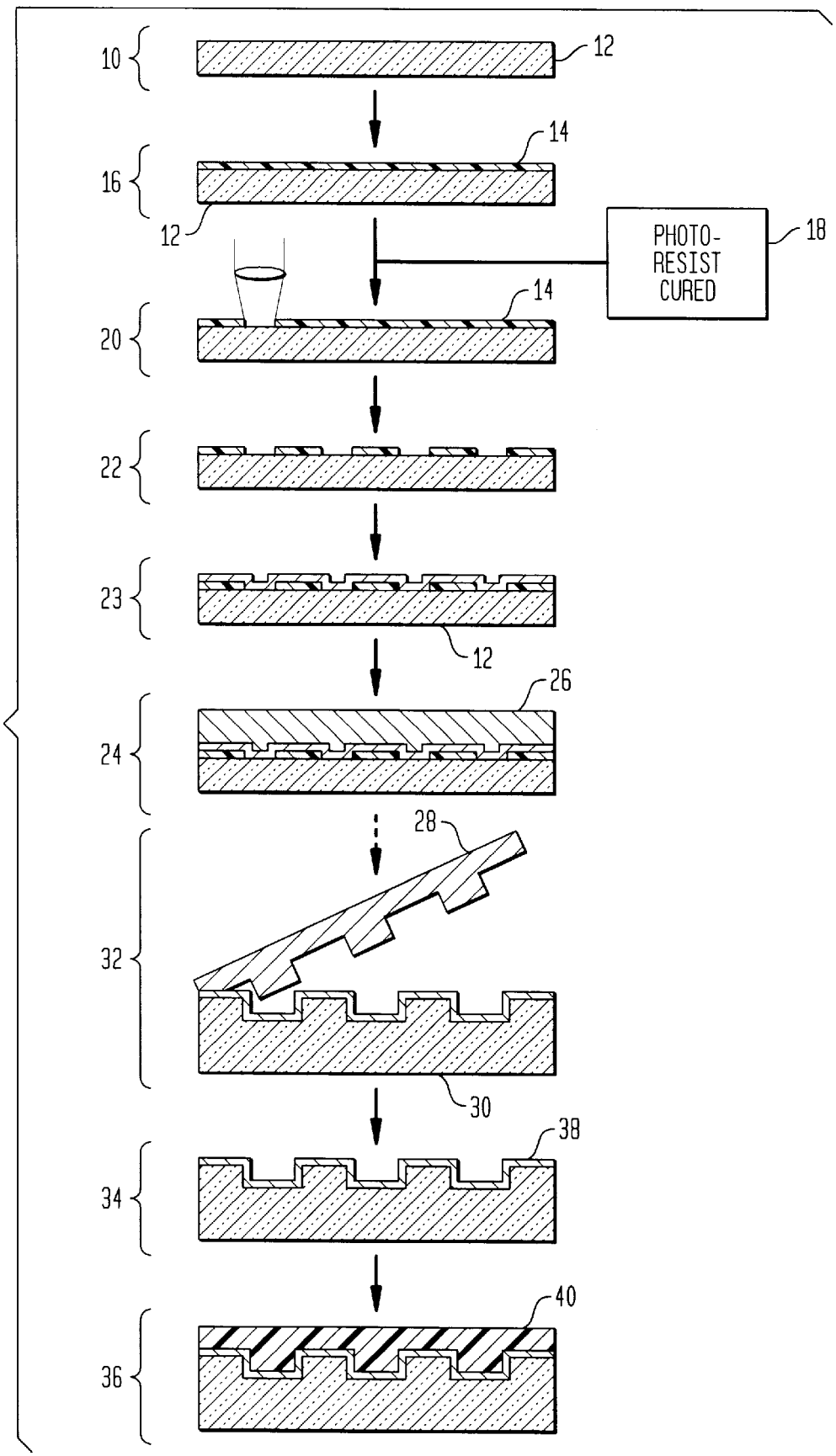
FIG. 1 shows an exemplary illustration of included in the manufacture of a compact disc.

Referring to FIG. 1, some of the basic steps are illustrated for the manufacture of compact discs. During a first step 10, a glass master disc or substrate 12 commonly referred to as a glassmaster template has its surface optically polished to prepare for application of chemical coatings. A photoresist coating layer 14 is next applied in step 16 to the polished glass surface of the glassmaster substrate 12. As would be understood by a person skilled in the art, an intermediate adhesive layer (not shown) which has a high affinity to the glass surface may be deposited prior to the photoresist layer in order to improve adherence of the photoresist layer to the glass. The adhesive layer is generally deposited on the surface of the substrate in an organic solvent prior to deposition of photoresist compositions.

Prior to cutting of the glassmaster, e.g., by laser recording or other known manner, the photoresist layer is cured (in step 18). Curing is typically accomplished by placing the glassmaster into a convection oven for a predetermined period of time to evaporate off the photoresist solvents. Alternatively, a hotplate that directs heat to the bottom of the photoresist coated glass substrate 12 may be utilized. The curing process is considered to be a critical step in the manufacture of the compact discs, since it is believed that uncured or partially cured polymer coatings may cause failure of the substrate during subsequent processing steps or use of the device.

After drying the photoresist layer 14, a laser beam may be used to cut a distinctive digital pattern into the photoresist layer (step 20). In a developing step 22, the irradiated portion of the polymer coating is then removed and the resultant surface pattern is silver or nickel coated. In step 24, the substrate 12 containing the resultant surface pattern is used to prepare a metal master 26, as would be understood by those skilled in the art. The metal master 26 is generally utilized to fabricate a stamper 28, which is capable of transferring the prescribed digital pattern to a transparent plastic substrate 30 (step 32). Once an impression is transferred to the plastic substrate 30, the plastic substrate is treated with a series of finishing steps 34, 36. This may include application of a reflective layer 38 by way of aluminum evaporation or sputtering in step 34. Once the reflective layer has been deposited, a protective film 40 is applied over the reflective layer (step 36) which fills in any impressions and allows for a uniform surface to be produced, thus completing the production of the compact disc.

Since it is suspected that one of the causes for glassmasters (and subsequently manufactured compact discs) that fail for "unknown" reasons is actually uncured or partially cured substrates that have been processed through glassmastering, the photoresist curing process is considered a particularly important step in the compact disc fabrication process. In addition, an ability to precisely detect when polymer coatings have been fully cured will increase the efficiency of the entire compact disc fabrication process. The present invention provides for the use of gas sensors in a feedback system to determine when the release of solvent vapors has reached a level indicative that the drying process for the photoresist layer is completed.

Figure 2:
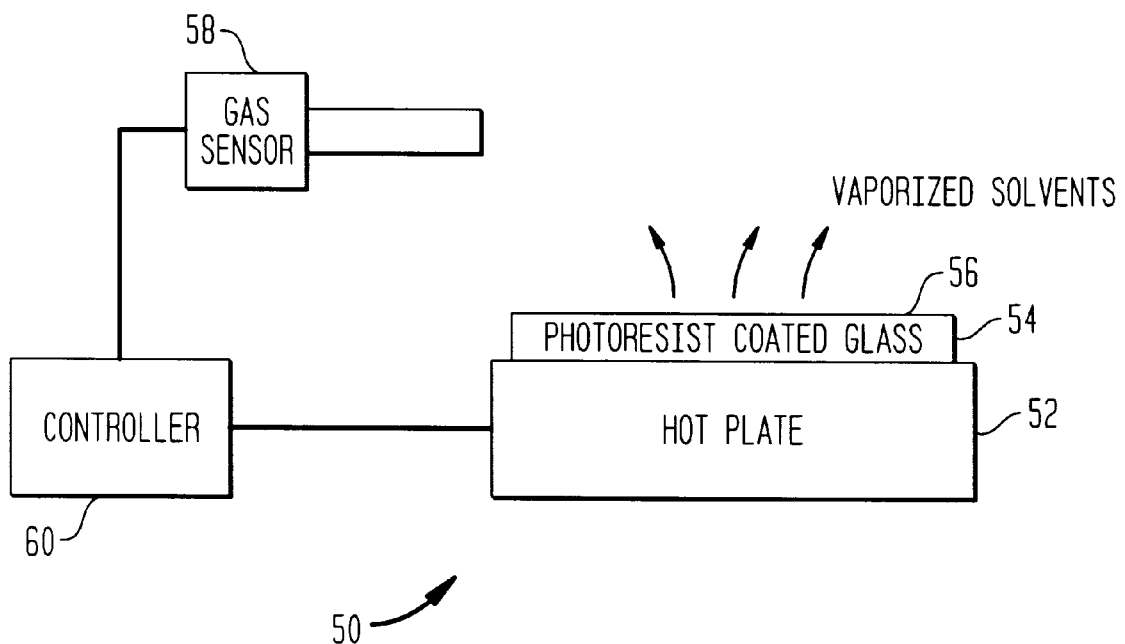
FIG. 2 shows one exemplary embodiment of the present invention including a hot plate heater curing apparatus with gas sensor feedback control.

Referring to FIG. 2, there is shown one exemplary embodiment of a curing system 50 utilizing a feedback mechanism to optimize the curing process. By controlling initial heating of the glassmaster substrate and controlling the curing/cool down characteristics, the present invention promotes optimum photoresist curing. As shown, the curing system 50 includes a heating apparatus, such as a hot plate 52. The hotplate directs heat to the bottom of a glass substrate 54 coated with a photoresist layer 56. A gas sensor 58 couples to the hotplate 52 through a controller 60 in a feedback loop, where the controller essentially acts as an interface between the gas sensor 58 and the hot plate 52.

In typical glassmastering operations for compact discs, a hotplate operates to supply a substantially constant temperature to the glassmaster substrate, for example 90 degrees Centigrade, and curing lasts for about 10 minutes with a minimum cool down time of 20 minutes. The present invention operates by measuring the quantity or concentration of solvent gases which are present during the curing operation and/or controlling the output of the heating source in accordance with these levels. The gas sensor can be programmed and/or wired to give an indication when a predetermined level or concentration of solvent gases is present (or not present). By utilizing feedback from the gas sensor it can be precisely determined when curing of the photoresist layer is completed, for example, when gases from the solvents being driven off or evaporated from the substrate are no longer present or have reached an acceptable minimal level.

Many commercially available gas sensors operate by giving an indication through their associated electronics of when hazardous levels or concentrations of gases are present in the surrounding atmosphere. Such indication may be in the form of a current or voltage output, or a triggering of a relay contact. The gas sensor of the present invention will preferably operate in a manner so as to give an indication when gases produced from the solvents are substantially no longer present. One such commercially available sensor capable of producing these types of outputs is the ISA-M Hazardous Gas Monitor/Alarm available from Emnet Corporation of Ann Arbor, Mich. This sensor is capable of being programmed for a number of typical sense calibrations for a wide variety of substances, such as general hydrocarbons and organic and inorganic solvents, as well as other suitable substances.

Accordingly, the gas sensor 58 will be programmed to give an indication when a predetermined level of solvent gas is present, thereby indicating a specified level of curing for the substrate. This indication can be an output in the form of a change in current or voltage level, the triggering of a relay contact, or other known manner of producing an indication signal. This output signal is then input to the controller 60 which operates to control the thermal output of the hot plate 52 or other heating apparatus. The controller 60 operates as a smart switch for the heating apparatus. Depending on the curing operation, upon receipt of an indication from the gas sensor 58 that the curing operation has been or is about to be completed, the controller 60 can implement a time delayed turn off of the hot plate 52 or alternatively generate signals to produce a controlled cool down at the hot plate for a specific period of time. Additionally, since measurable solvent levels may not be present at the gas sensor 58 at the outset of the curing process, the controller may also incorporate a time delay for receipt of indications from the gas sensor which would in turn trigger a premature turn off of the heating apparatus. Accordingly, the controller 60 may be outfitted with a programmable digital processor and/or other circuitry for carrying out such functionality, as would be understood by a person skilled in the art. The controller 60 may also operate to precisely control the heat level produced at the glassmaster substrate. This could be accomplished, for example, by adjusting the level of analog or digital signals output form the controller to the heating apparatus.

As would be understood, the gas sensor 58 will typically be placed in close proximity to the photoresist coated substrate 54 so as to give an accurate reading of the concentration of vaporized solvents. Accordingly, the gas sensor may be located within a chamber or other enclosed area. Alternatively, if the gas sensor is located outside of the chamber or other enclosed area, samples of the gases would be periodically drawn from the chamber by methods understood to those skilled in the art.

Figure 3:
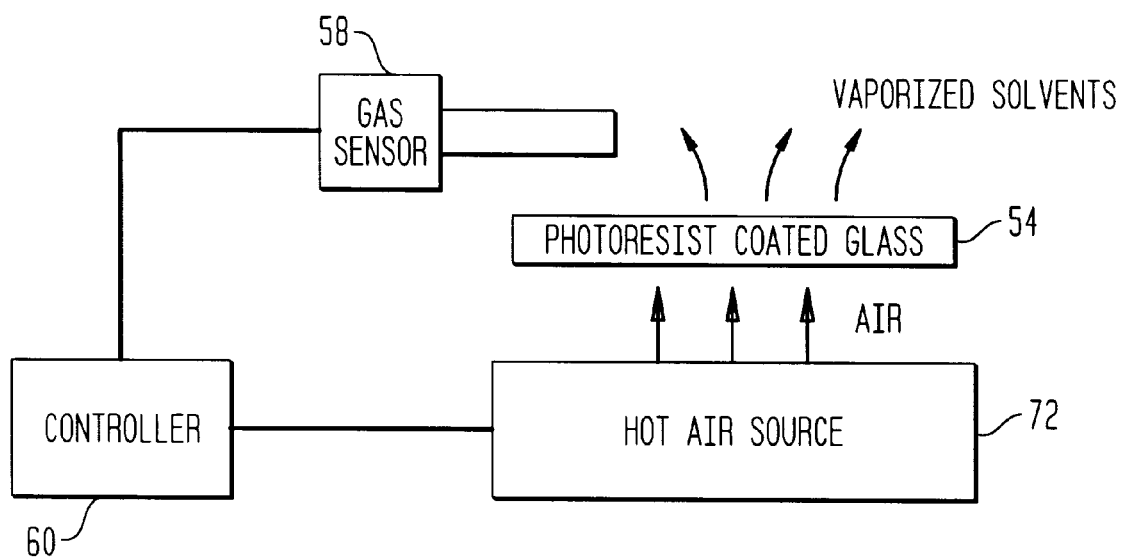
FIG. 3 shows another exemplary embodiment of the present invention including a hot air drying system equipped with gas sensor feedback control.

Referring to FIG. 3, an alternate embodiment of a curing system 70 in accordance with the present invention is shown. As with the embodiment shown in FIG. 2, the system includes a gas sensor 58 coupled through a controller 60 to a heating apparatus 72. In the embodiment of FIG. 3, however, the preferred heating apparatus 72 is a hot air source for curing the photoresist coated glass substrates 54. In the exemplary embodiment, clean class 100 air or better, heated to a temperature of 90 degrees Centigrade, for example, is produced from a blower or other suitable device. The air strikes the bottom of the photoresist coated glass substrate 54 for timed or feedback controlled curing in a similar fashion to that explained in FIG. 2. An advantage of this methodology is that the curing takes place in a non-contact manner, as with a convection oven, but the air is directed to the area requiring curing similarly to the use of the hot plate. As with the hot plate system, the gas sensor and the substrate to be cured will typically be located within a chamber. Alternatively, it may be necessary to draw samples of gases from the chamber by way of a fan or other suction-type device.

Figure 4:
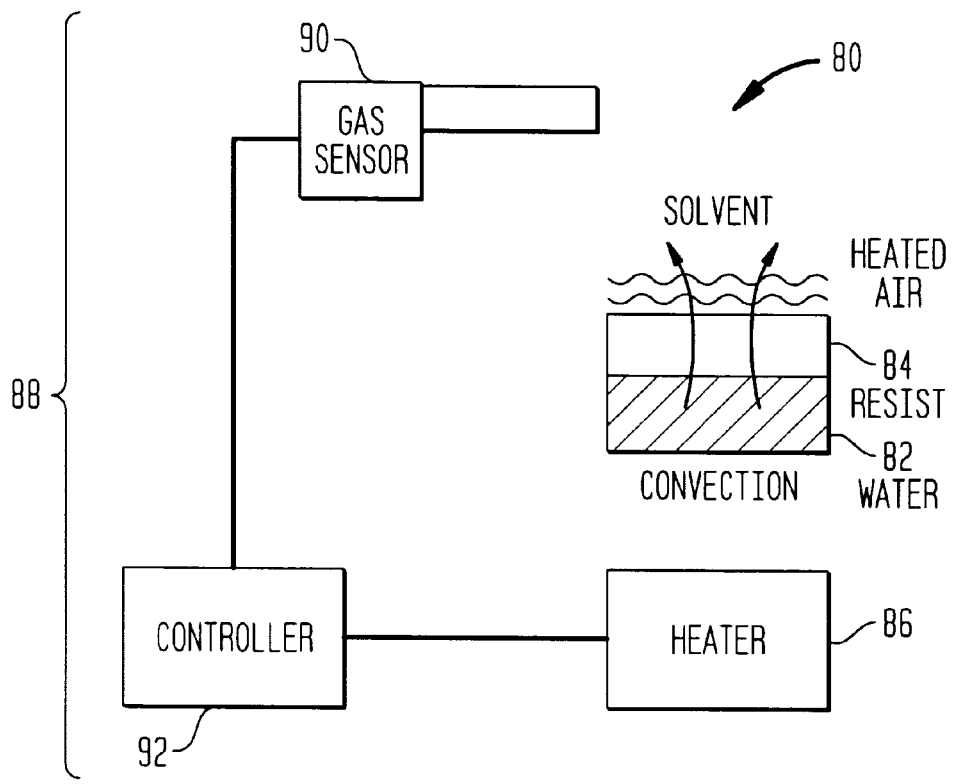
FIG. 4 shows an exemplary embodiment of the present invention as used in the curing of substrates for the semiconductor fabrication industry.

Like the compact disc manufacturing industry, the semiconductor fabrication industry makes use of highly polished surface substrates such as silicon, alumina and quartz having photoresist layers deposited thereon. A barrier layer is typically applied over the substrate layer, where the photoresist is cured by hot plate, oven or other similar heating method. In order to improve the results of the curing process found in semiconductor fabrication, the gas sensor feedback system of the present invention may be utilized. FIG. 4 shows one embodiment for a heating system 80, using the methodology of the present invention, for use in the semiconductor manufacturing industry. As shown, a semiconductor wafer 82 has its resist layer 84 being cured and the solvents being evaporated through a convection heating process. In a similar fashion to the embodiments described with respect to FIGS. 2 and 3, the embodiment of FIG. 4 includes a heating apparatus 86 which couples to a gas sensor feedback system 88. As shown, the feedback system 88 similarly includes a gas sensor 90 having suitable indication circuitry, along with a controller 92 coupled in a feedback loop. In typical operation, during the curing operation the gas sensor 90 provides a signal or signals indicative that the solvent vapor is no longer detected. Upon detection of the signal from the gas sensor 90, the controller 92 can then trigger the application of class 100 cool air.

Figure 5:
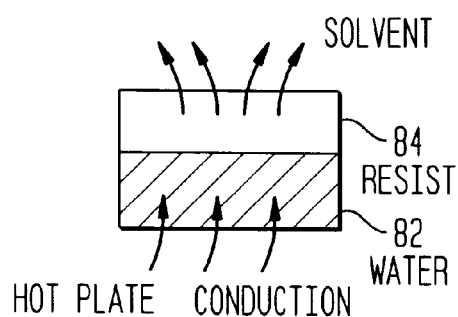
FIG. 5 shows curing of an exemplary semiconductor wafer using conduction.

The present invention is also applicable for use in semiconductor curing process utilizing a conduction type heating methodology 96 as shown in FIG. 5. The feedback system of the invention is advantageous for use in these semiconductor curing operations, since it ensures curing of photoresist 84 coated semiconductor substrates 82 within a minimum process time.

As some of the exemplary embodiments of the present invention were focused on the curing of photoresist utilized in the glassmastering process for compact discs, the following is a more detailed description of the glassmaster production process focusing on the solvent drying of the coated substrate. The solvent presence is due to the type coating processes used.

In one preferred embodiment the material selected to form the intermediate adhesive layer for a glassmaster comprises titanium acetylacetonate. It is well suited for this purpose since the titanium portion of this compound has a high affinity for glass and the acetylacetonate interacts well with the photoresist polymer. The titanium compound is dissolved in isopropyl alcohol in a ratio of 1:3. This solution is then diluted in methylisobutylketone and is deposited onto a rotating disc forming a layer of this adhesive material on the surface of the glass. The solvents are evaporated in the downward stream of dust-free air. All the solvents and dissolved titanium acetylacetone solutions are filtered prior to deposition to remove any particles greater than 0.2 $\mu$m in size. The resulting adhesive layer formed by this method will be only one molecule thick.

The photoresist coating composition comprises a polymer and a photosensitive compound. In this example the polymeric material is a modified form of novolak, comprising a polymer of phenol formaldehyde and cresol formaldehyde and the photosensitive compound is napathoquinone diazide. Irradiation of the orthonaphtoquinone diazide yields a short-lived ketene which hydrolyses to a base soluble indene carboxylic acid. Use of the diazide sensitizer provides a media which can be etched with light. A base wash of the irradiated photoresist will provide a pattern for the glassmaster which will be transferred to a compact disc. The photoresist composition is diluted with methylisobutyketone to a concentration of 8.5 to 9% by volume.

A measured quantity of the diluted photoresist is dropped at the center of a rotating disc. Due to the high rotational speed the diluted photoresist composition will be evenly distributed on the disc. The methylisobutylketone will be evaporated in the downward stream of dust free air. These examples of coating the glass plate are not to be limiting examples of the adhesive and photoresist coating of a glass disc or any electronic substrate surface. The purpose of providing these examples is to demonstrate how solvents become entrapped in each step of the coating process. Solvents which may be used for substrate coating are any organic solvents alone or in combination with one another which will provide good coating of the adhesive, polymer photosensitizer and any additional layers necessary for the production of the electronic device with compact discs. The glassmasters that fail are believed to be uncured or partially cured substrates, which still contain residual solvents after processing.

The above described exemplary chemical compositions have been found to function suitably in connection with the gas sensor feedback system of the present invention. It will be understood, that the exact conditions for curing, e.g. temperatures and times intervals, will be determined by the selection of the solvent and coating materials used to produce the coated substrate. The principles of the present invention are, however, generally applicable to all such materials. As would be understood, the invention is by no means limited to the described exemplary embodiments. Any system which can supply sufficient heat to dry the coating or coating can be used with a gas detection feedback system to enhance efficient completion of the drying process.

From the above, it should be understood that the embodiments described in regard to the examples, are merely exemplary and that a person skilled in the art may make variations and modification to the demonstrated embodiments without departing from the spirit and the scope of the invention. Variations of the heating systems and locations of the gas sensors and methods for obtaining and analyzing the gas samples are intended to be included within the scope of the invention as defined in the appended claims.

We claim:

1. A system for thermal curing of polymer coatings deposited on substrates, said thermal curing implemented by a heating device directing heat toward said substrates, said system comprising:

at least one gas sensor for detecting concentrations of vapors emitted from said substrates undergoing curing, said gas sensor operable to generate an indication when said concentrations of vapors reach a predetermined level; and a controller coupled to said gas sensor and said heating device, said controller operable to receive said indication from said gas sensor and adjust heating characteristics of said heating device in response to receipt of said indication.

2. The system of claim 1, wherein said substrates include glassmasters for use in the manufacture of compact discs.

3. The system of claim 1, wherein said substrates include semiconductor wafers.

4. The system of claim 1, wherein said controller is operable to implement a controlled cool down period at said heating device in response to said indication from said gas sensor.

5. The system of claim 1, wherein said controller is operable to implement a time delayed turn off of said heating device upon receipt of said indication from said gas sensor.

6. The system of claim 1, further including said heating device, wherein said heating device is selected from the group consisting of: convection oven, hot plate and hot air flow system.

7. The system of claim 1, wherein said thermal curing takes place within an enclosed area, said gas sensor located within said enclosed area.

8. The system of claim 1, wherein said thermal curing takes place within an enclosed area and said gas sensor is located outside of said enclosed area, wherein samples are drawn from said enclosed area and input to said gas sensor.

9. The system of claim 1, wherein said gas sensor is operable to detect the presence of organic solvents used for the polymer coating.

10. The system of claim 1, wherein said polymer coating comprises a photoresist composition.

11. The system of claim 1, wherein said indication is generated when a surrounding environment proximate said substrates is substantially free from said vapors emitted during curing.

12. An apparatus for controlling thermal curing of polymer coatings deposited on glassmasters used in the fabrication of compact discs, said thermal curing implemented by a heating device directing heat toward said glassmasters, said apparatus comprising:
   a feedback mechanism coupled to said heating device, said feedback mechanism including at least one gas sensor for detecting concentrations of vapors emitted from said glassmasters undergoing curing, said feedback mechanism operable to adjust the output of said heating device in response to an indication from said gas sensor that said concentrations of vapors emitted from said glassmasters have reached a predetermined level.

13. The apparatus of claim 12, wherein said feedback mechanism is operable to implement a controlled cool down period t said heating device in response to said indication from said gas sensor.

14. The apparatus of claim 12, wherein said feedback mechanism is operable to implement a time delayed turn off of said heating device upon receipt of said indication from said gas sensor.

15. The apparatus of claim 12, wherein said gas sensor is operable to detect the presence of organic solvents used for the polymer coating.

16. The apparatus of claim 12, wherein said polymer coating comprises a photoresist composition.

17. The apparatus of claim 12, wherein said indication is generated when a surrounding environment proximate said glassmasters is subsequently free from said vapors emitted during curing.

18. A system for thermal curing of polymer coatings deposited on a substrate selected from the group consisting of glassmasters and semiconductor wafers, said thermal curing implemented by a heating device directing heat toward said substrates, said system comprising:
   at least one gas sensor for detecting concentrations of vapors emitted from said substrates undergoing curing, said gas sensor operable to generate an indication when said concentrations of vapors reach a predetermined level; and
   a controller coupled to said gas sensor and said heating device, said controller operable to receive said indication from said gas sensor and adjust heating characteristics of said heating device in response to receipt of said indication.

19. A system for thermal curing of a photoresist composition deposited on substrates, said thermal curing implemented by a heating device directing heat toward said substrates, said system comprising:
   at least one gas sensor for detecting concentrations of vapors emitted from said substrates undergoing curing, said gas sensor operable to generate an indication when said concentrations of vapors reach a predetermined level; and
   a controller coupled to said gas sensor and said heating device, said controller operable to receive said indication from said gas sensor and adjust heating characteristics of said heating device in response to receipt of said indication.

20. A system for thermal curing of polymer coatings deposited on substrates, said thermal curing implemented by a heating device directing heat toward said substrates, said system comprising:
   at least one gas sensor for detecting concentrations of vapors emitted from said substrates undergoing curing, said gas sensor operable to generate an indication when surrounding environment proximate said substrates is substantially free from said vapors emitted during curing; and
   a controller coupled to said gas sensor and said heating device, said controller operable to receive said indication from said gas sensor and adjust heating characteristics of said heating device in response to receipt of said indication.

21. An apparatus for controlling thermal curing of polymer coatings deposited on glassmasters used in the fabrication of compact discs, said thermal curing implemented by a heating device directing heat toward said glassmasters, said apparatus comprising:
   a feedback mechanism coupled to said heating device, said feedback mechanism including at least one gas sensor for detecting concentrations of vapors emitted from said glassmasters undergoing curing, said feedback mechanism operable to adjust the output of said heating device in response to an indication from said gas sensor that said concentrations of vapors emitted from said glassmasters have reached a predetermined level, wherein said indication is generated when a surrounding environment proximate to said glassmasters is substantially free from said vapors emitted during curing.

* * * * *